(12) United States Patent
Keropian

(10) Patent No.: US 7,451,767 B2
(45) Date of Patent: *Nov. 18, 2008

(54) SLEEP APPLIANCE

(76) Inventor: Bryan Keropian, 18607 Ventura Blvd., #206, Tarzana, CA (US) 91356

( * ) Notice: Subject to any disclaimer, the term of this patent is extended or adjusted under 35 U.S.C. 154(b) by 0 days.

This patent is subject to a terminal disclaimer.

(21) Appl. No.: 11/165,641

(22) Filed: Jun. 23, 2005

(65) Prior Publication Data
US 2006/0289013 A1 Dec. 28, 2006

(51) Int. Cl.
*A61F 5/56* (2006.01)

(52) U.S. Cl. .................. 128/848; 128/859; 128/860; 128/861; 128/862; 602/902; 433/6; 433/7; 433/8

(58) Field of Classification Search .............. 128/848, 128/859–862; 602/902; 433/6, 7, 8
See application file for complete search history.

(56) References Cited

U.S. PATENT DOCUMENTS

| | | | |
|---|---|---|---|
| 2,705,006 A | 6/1955 | Cettel et al. | |
| 3,132,647 A | 4/1962 | Cornielllo | |
| 3,312,216 A | 7/1963 | Wallshien | |
| 3,871,370 A | * 3/1975 | McDonald | 128/860 |
| 4,273,530 A | 6/1981 | Broussard | |
| 4,299,568 A | 11/1981 | Crowley | |
| 4,468,196 A | 8/1984 | Keller | |
| 4,669,459 A | 6/1987 | Spiewak et al. | |
| 4,676,240 A | 6/1987 | Gardy | |
| 4,901,737 A | * 2/1990 | Toone | 128/848 |
| 4,976,614 A | 12/1990 | Tepper | |
| 4,986,283 A | 1/1991 | Tepper | |
| 5,096,416 A | 3/1992 | Hulsink | |
| 5,376,001 A | 12/1994 | Tepper | |
| 3,277,892 A | 10/1996 | Tepper | |
| 5,570,704 A | 11/1996 | Buzzard | |

(Continued)

FOREIGN PATENT DOCUMENTS

DE 19503288 7/1996

(Continued)

OTHER PUBLICATIONS

Bryan Keropian, DDS, Declaraction dated May 9, 2007 with two attached photographs.

*Primary Examiner*—Patricia Bianco
*Assistant Examiner*—Nihir Patel
(74) *Attorney, Agent, or Firm*—Lewis Brisbols Bisgaard & Smith LLP; Sanford Astor (57) ABSTRACT

A dental oral appliance for use with patients who suffer with sleep disorders, to reduce or eliminate snoring and to open the airway for a sleeping individual who suffers with obstructive sleep apnea. The appliance covers the inside (lingual) of the upper teeth and has an open palate. Retention for the appliance is provided by either clasps placed over the upper right and left molars and a retainer in the anterior area or by an occlusal coverge of the upper teeth. A raised incisor ramp that extends from the incisal tip (biting edge) of the incisors toward the lingual, or posterior raised ramps, separate the posterior teeth to reduce spasm on the temporalis muscle. A transverse, transpalatal ramp, which extends from the inside (lingual) of the upper right molars to the inside of the upper left molars, covers the tongue and holds it down, opening the airway.

14 Claims, 7 Drawing Sheets

U.S. PATENT DOCUMENTS

| | | |
|---|---|---|
| 5,580,243 A | 12/1996 | Bloore |
| 5,607,300 A | 3/1997 | Tepper |
| 5,915,385 A * | 6/1999 | Hakimi ........................ 128/848 |
| 6,408,852 B2 | 6/2002 | Tielemans |
| 6,467,484 B1 * | 10/2002 | De Voss ........................ 128/848 |
| 6,766,802 B1 * | 7/2004 | Keropian ...................... 128/848 |
| 2001/0027793 A1 | 10/2001 | Tielemans |
| 2002/0189620 A1 | 12/2002 | L'Estrange et al. |
| 2004/0045556 A1 | 3/2004 | Nelson et al. |
| 2006/0130850 A1 | 6/2006 | Chen |

FOREIGN PATENT DOCUMENTS

| | | |
|---|---|---|
| DE | 19512761 | 10/1996 |
| DE | 10011687 | 11/2000 |

* cited by examiner

SLEEP APPLIANCE

BACKGROUND OF THE INVENTION

The invention described in this application is an improvement over the device described in my U.S. Pat. No. 6,766,802, issued on Jul. 27, 2004.

As stated in my patent referenced above, it has been estimated that ninety million American adults and children snore and that one in every ten adults snores. Snoring can have serious medical consequences for some people. Snoring is the first indication of a potentially life-threatening sleep disorder called Obstructive Sleep Apnea. If not diagnosed or if left untreated, Obstructive Sleep Apnea could result in severe medical consequences such as systemic high blood pressure, cardiovascular disease and even sudden death.

Snoring is caused by vibration of the tissues due to air turbulence as the airway narrows and may be a sign that a patient is suffering from apnea. But not all snorers suffer from apnea. Snoring can be categorized by its severity. There is the snorer who snores but experiences no physical problems. Then there is the snorer who suffers from apnea, or the snorer who suffers from upper airway resistance. In some of these people, though they may not actually experience apneic episodes, their snoring is so loud and their breathing so labored, that it still wakes them, and their partners, numerous times throughout the night.

Many spouses, partners and/or children suffer through the night from the annoying noise of the snorer. Snoring not only disturbs the sleeping pattern of the snorer himself, it is also disruptive to the family life by causing lack of sleep to all involved. This leaves all involved unrefreshed, tired and sleepy throughout the day. It can cause sleepiness while driving, reading, working or doing other tasks.

A broad variety of intra-oral and dental appliances and devices are now available to treat a patient for snoring. Some known oral devices for treating snoring and obstructive sleep apnea are worn inside of the mouth and work by repositioning of the jaw, moving the mandible, lifting the soft palate or moving the tongue forward. The various classes of treatment devices that now exist include mandibular advancers and tongue advancers. These appliances work by advancing the tongue and soft palate away from the back wall of the throat. Other methods used to treat snoring include controlled positive air flow pressure systems also known as CPAP which require a nose mask and which are quite uncomfortable.

Other treatments for snoring include various surgeries, which are drastic steps to take to attempt to cure the problem however snoring can be so disruptive to a person's life and relationships, that some sufferers resort to surgery.

Another device which has been known is described in U.S. Pat. No. 6,467,484 to De Voss. The device of De Voss fits entirely over the teeth and presses against the inside of the mouth and the gums, making it uncomfortable for the user to wear. In addition, the device is held in the user's mouth only by pressure against the teeth from the groove in the U-shaped member that fits over the teeth. If that pressure releases for any reason, such as material fatigue, the entire device can fall off of the teeth, which could be a very dangerous situation.

The devices described in my previously issued U.S. Pat. No. 6,766,802, issued on Jul. 27, 2004, were held in place by retainer wires and clasps. In addition, a transverse or transpalatal bar held the tongue down to open the air space.

BRIEF DESCRIPTION OF THE INVENTION

The sleep appliance of this invention is a dental oral appliance for use with patients who suffer with sleep disorders. Primarily it is designed to reduce or eliminate snoring and to open the airway for a sleeping individual who suffers with obstructive sleep apnea.

One embodiment of the appliance is physically designed similar to an upper (maxillary) orthodontic retainer, commonly called a Hawley retainer. It covers the inside (lingual) of the upper teeth and has an open palate (nothing covering the middle area of the palate.) Retention (holding ability) for the appliance is provided by clasps. Another embodiment utilizes acrylic fittings which hold the appliance in place in the same manner as an occlusal night guard.

In the anterior area, there is a retainer wire or acrylic fittings to hold the anterior teeth in place or to move them backwards (inward towards the palate [lingually]).

In one embodiment, in the anterior area over some or all of the upper incisors is a raised strip or ramp that extends from the incisal tip (biting edge) of the incisors toward the lingual. It extends back from the middle of the central incisors (where they meet or touch each other) to the middle of the palate. This raised anterior area is to disclude or separate the posterior teeth. The net effect is to reduce spasm on the temporalis muscle and aid in reducing migraine and chronic tension headache pain that comes from bruxing and clenching (squeezing teeth together with potentially up to thousands of pounds of pressure). Nocturnal bruxing and clenching are the cause of pain coming from the spasmed temporalis muscle.

In an additional embodiment there is no anterior ramp. The upper and lower teeth are separated by raised posterior ramps. This embodiment allows more room for the tongue to come forward, if desired.

There is a transverse strip, a transpalatal bar, that extends from the inside (lingual) of the upper right molars to the inside of the upper left molars. This transverse strip extends from the right to the left and covers the tongue, holding it down.

To understand the effectiveness of the appliance, the mechanism of snoring and obstructive sleep apnea must be understood. While we sleep, the tongue falls back and up towards the palate and it partially or completely obstructs or closes the airway path. This results in snoring, obstructive sleep apnea, or Upper Airway Resistance Syndrome. The medical treatment for these maladies range from medication to a C-PAP (Continuous Positive Airway Pressure) machine. The C-PAP is nearly 100% successful when utilized. Unfortunately, the non-compliance for C-PAP use ranges from 50% to 80% depending where one searches in the literature. The American Association of Sleep Medicine designated dental sleep appliances as the number one alternative to CPAP. The sleep appliance of this invention is designed to treat the problem of tongue blockage when sleeping. It works by utilizing several factors. First, it changes the vertical dimension (height of the opening or separation of the teeth). This results in an increased opening of the airway. Second, the strip that runs transverse along the back of the appliance effectively holds the tongue down and does not allow it to fall back and block the airway opening.

OBJECTS OF THE INVENTION

Accordingly, several objects and advantages of the invention are as follows:

It is an object of this invention to provide a simple device to prevent or reduce snoring as well as Obstructive Sleep Apnea.

It is another object of this invention to provide a device, easily applied and easily tolerated, which will substantially prevent snoring.

Further objects and advantages will become apparent from a consideration of the following description and drawings.

DETAILED DESCRIPTION OF THE INVENTION

Figure 1:
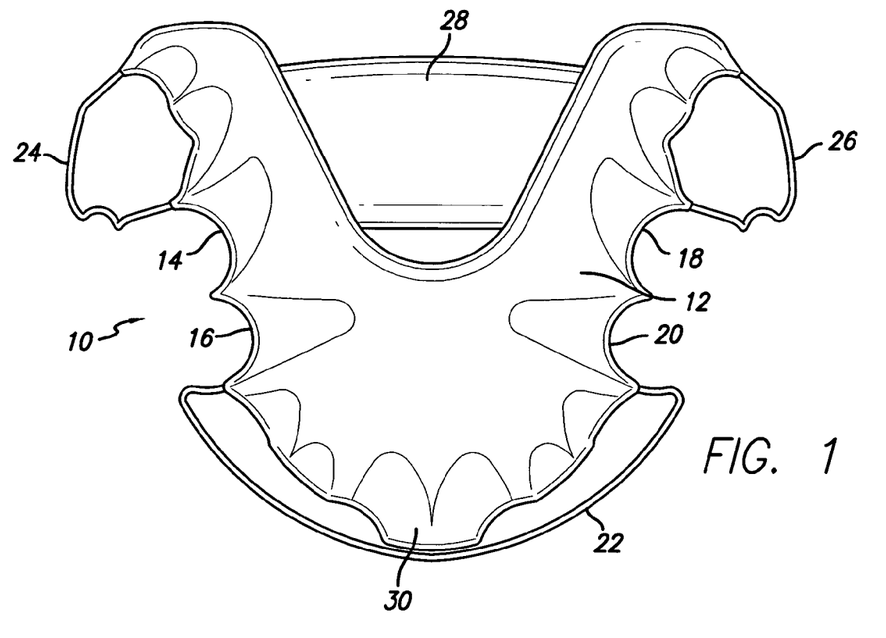
FIG. 1 is a top view of the sleep appliance described in my earlier issued patent.
Figure 2:
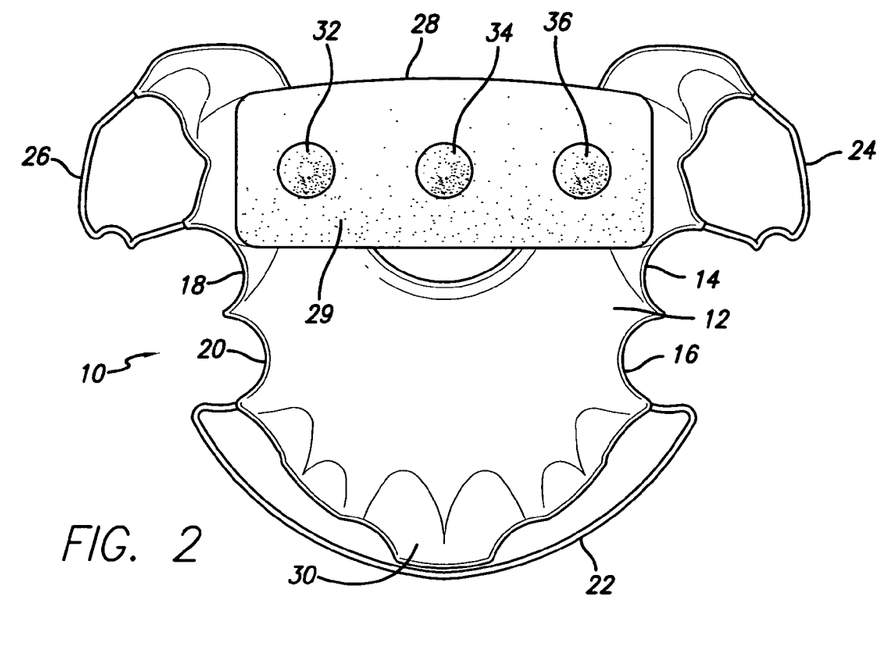
FIG. 2 is a bottom view or the device of this invention having posterior projections.

Referring now to FIGS. 1 and 2, FIG. 1 shows the sleep appliance described in my previously issued patent and FIG. 2 shows one embodiment of the sleep appliance of this invention. Shown in both FIGS. 1 and 2 are appliance 10 having a body 12 which fits adjacent the inside of the upper teeth of the person wearing it. Body 12 fits snugly against the palate, or roof of the mouth. Body 12 is generally U-shaped, however it has a series of recesses 14, 16, 18 and 20, as well as additional recesses as needed, to fit the body 12 against the lingual side of the upper teeth, covering the inside of the upper teeth. The device is custom fit to each patient by making a mold or dental impression of the inner surface of the upper teeth and the palate. The appliance is then made from the mold using a clear acrylic plastic commonly used for dental appliances.

Appliance 10 is held in place by an anterior retainer 22 and two posterior retaining clasps 24 and 26. Anterior retainer 22 is a wire, usually made of metal and extends from eye-tooth to eye-tooth, #6-#11. Retainer wire 22 is similar to the standard wire used on orthodontic appliances to hold the anterior teeth in place or to move them backwards, inward ([lingually) towards the palate. These wires are usually made of stainless steel.

Appliance 10 is further held in place by two posterior retaining clasps 24 and 26, commonly called Adams clasps, placed over upper right and left molars, preferably the first molars. Clasps 24 and 26 are also wires, usually made of metal, and usually stainless steel. Retainer wires 22, 24 and 26 hold appliance 10 securely in place.

Transverse strip or transpalatal bar 28 extends from the inside (lingual) of the upper right molars to the inside of the upper left molars, preferably the second molars. Transpalatal bar 28 extends from the right to the left side of appliance 10, covering the tongue, acting as a tongue depressor, holding down the tongue, leaving an open air passage. As shown in FIG. 2, a plurality of posterior projections 32, 34 and 36 have been added to the bottom 29 of transpalatal bar 28 to further press the tongue down and thus further open the airway. Posterior projections 32, 34 and 36 may be from about 1 mm to about 6 mm long depending upon the needs of the patient. While three projections are shown and they are cylindrical, any number, from about 2 to about 12 projections may be used and they may be any shape, such as rectangular, conical, oval, or any other shape.

In the anterior area over the upper central incisors there is a raised incisor strip or ramp 30 that extends from the incisal tip (biting edge) of two or more of the incisors toward the lingual. Strip 30 extends back from the middle of the central incisors, where they meet or touch each other, to the middle of the palate. This raised strip 30 acts as a bite discluder, separating the posterior teeth, which reduces spasm on the temporalis muscle and aids in reducing migraine and chronic tension and headache pain, which come from a spasmed temporalis muscle.

Strip 30 is preferably from about 3 mm to about 5 mm thick in order to separate the posterior teeth. Body 12, tongue depressor 28, strip 30 and projections 32, 34 and 36, are preferably made of a clear acrylic plastic commonly used for dental appliances, but could be made from other plastics or rubber material.

Figure 3:
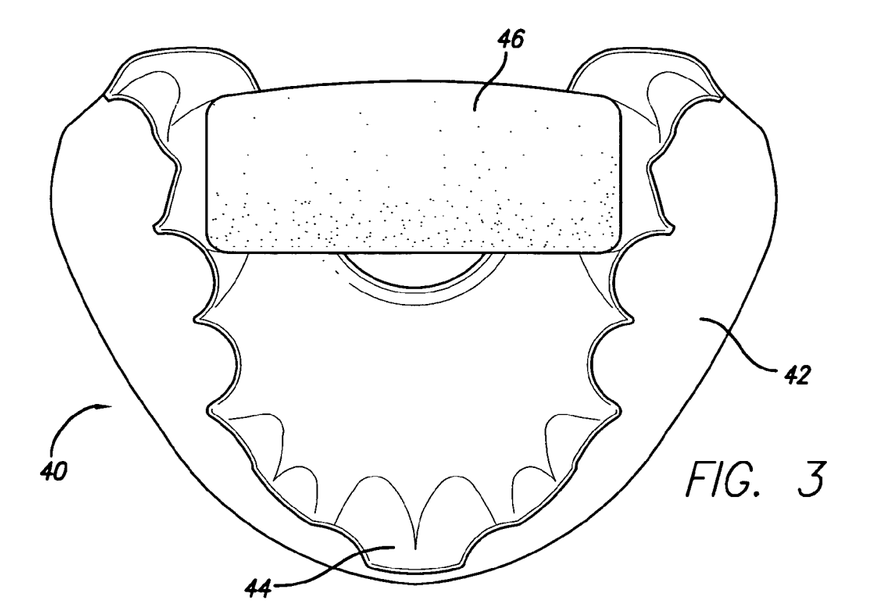
FIG. 3 is a bottom view with no wires being all acrylic.
Figure 4:
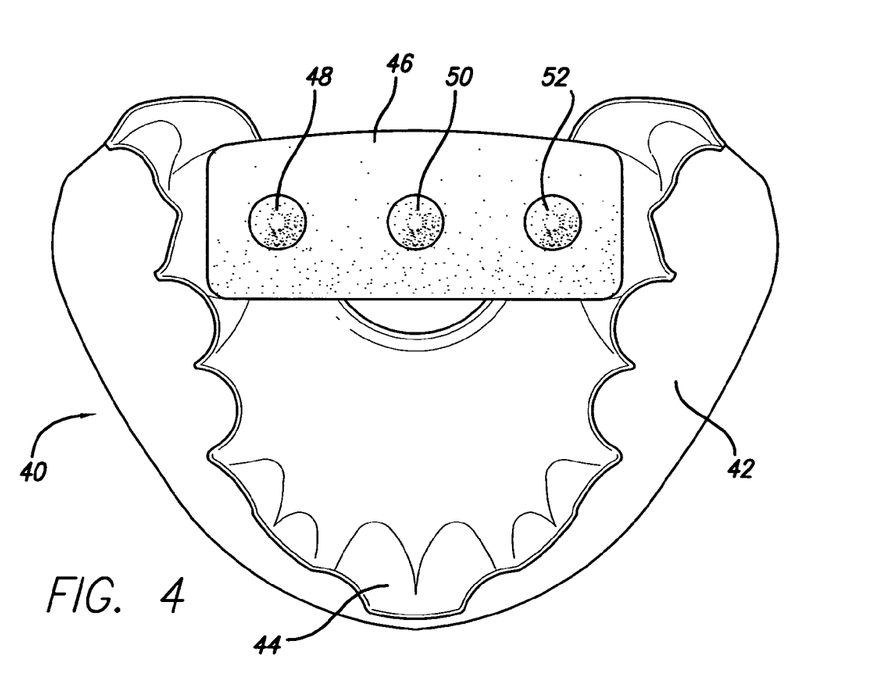
FIG. 4 is a bottom view of, all acrylic, with projections.

In another embodiment shown in FIGS. 3 and 4, there is shown sleep appliance 40 which has no wire retainer or wire clasps. Body 42 is made entirely of an acrylic plastic, commonly used for dental devices, and is custom fitted to fit over the wearer's posterior teeth in the same manner as an occlusal night guard which uses an occlusal coverage. The occlusal coverage holds appliance 40 firmly onto the posterior teeth.

There is a raised anterior strip 44, similar to that shown in FIGS. 1 and 2, to help separate the posterior teeth. A transpalatal bar 46 is attached to body 42 adjacent the molars to hold the tongue down and open the airway. The embodiment of FIG. 4 has projections 48, 50 and 52, to hold the tongue down even further, if necessary to create a wider, more open airway.

Figure 5:
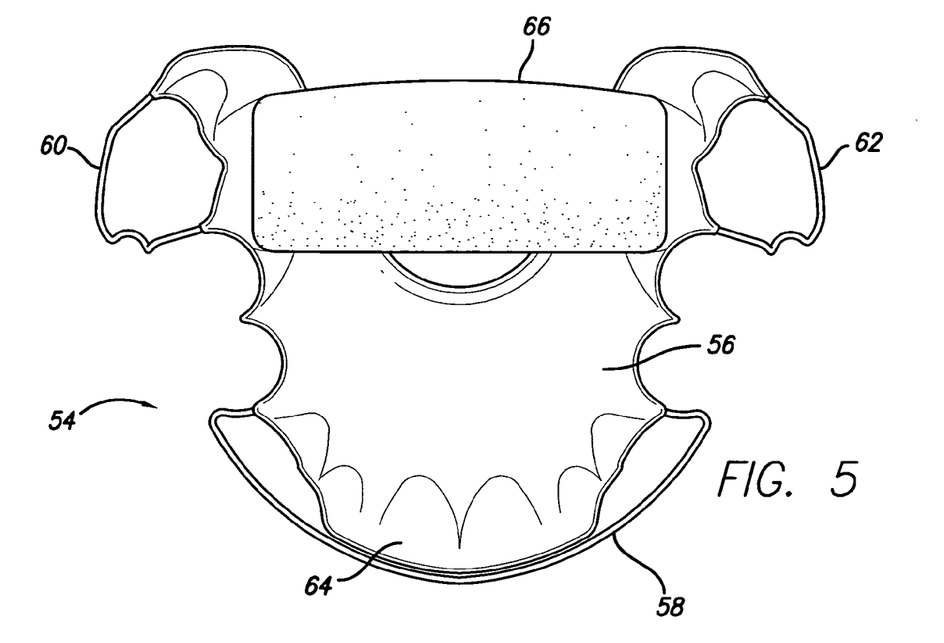
FIG. 5 is a bottom view of an embodiment with an anterior raised acrylic ramp.
Figure 6:
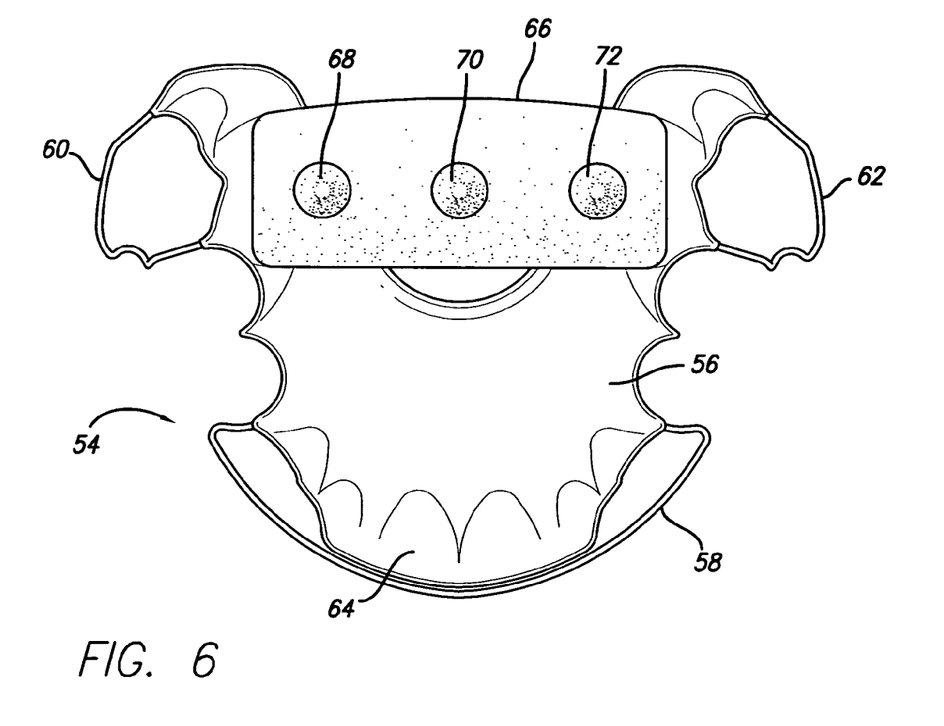
FIG. 6 is a bottom view of the embodiment of FIG. 5 with projections on the transpalatal bar.

Referring now to FIGS. 5 and 6 there is shown another embodiment of a sleep appliance 54, having a body 56. Appliance 56 is held in place as shown in FIGS. 1 and 2, by anterior retainer 58 and two posterior retaining clasps 60 and 62.

Raised anterior strip or ramp 64 is wider than the anterior ramp shown in FIGS. 1 and 2, as it includes and extends from all four maxillary teeth. The beneficial effect of making anterior ramp 64 include all four maxillary teeth is that it distributes the load over four teeth instead of just two teeth, reducing the load on each tooth.

Transpalatal bar 66 extends from the posterior molars on one side to the other, to hold the tongue down and increase the airway passage. In FIG. 6, ramp 66 has a plurality of raised projections 68, 70 and 72, which may be added to further push the tongue down and increase the airway passage.

Figure 7:
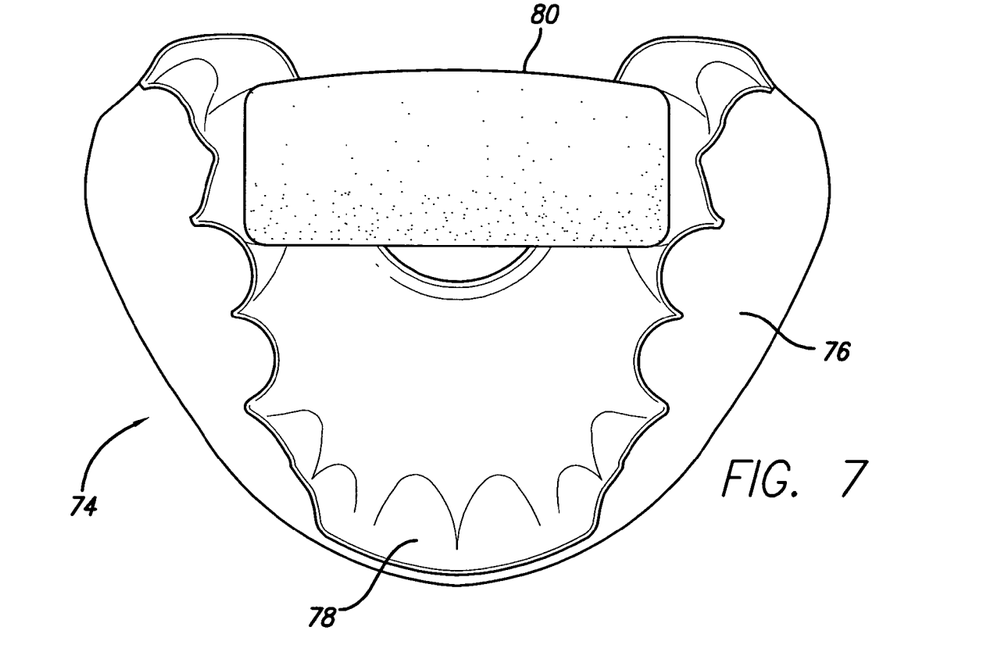
FIG. 7 is a bottom view of the embodiment of FIG. 3 with a wider ramp.
Figure 8:
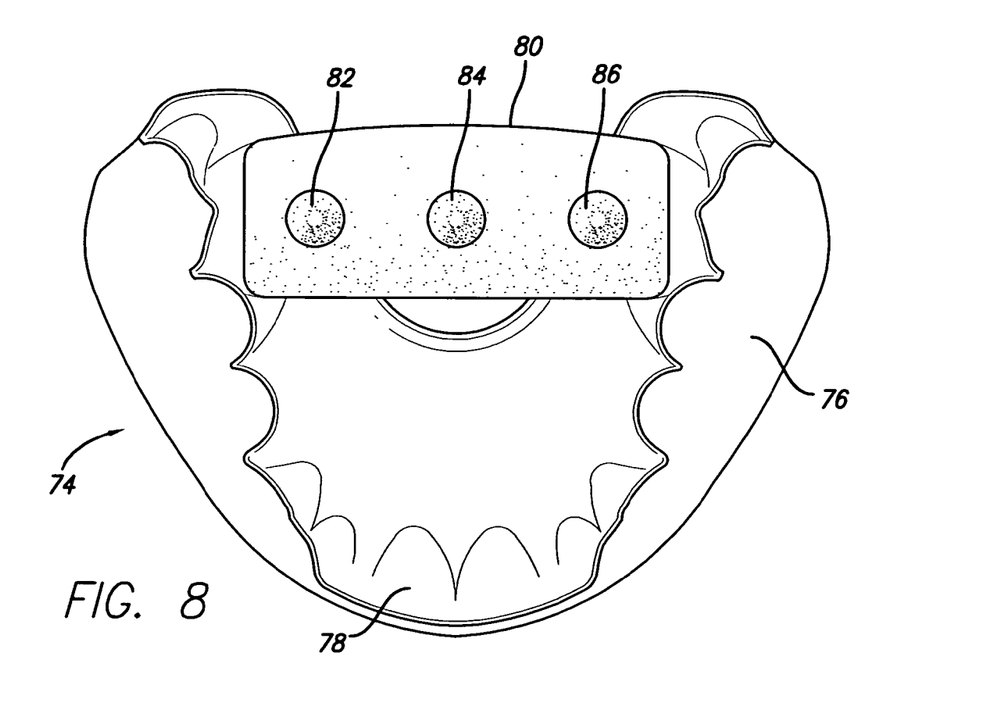
FIG. 8 is a bottom view of the embodiment of FIG. 7 with projections on the transpalatal bar.

Referring to FIGS. 7 and 8, there is shown the sleep appliance shown in FIGS. 3 and 4, but with the wider anterior ramp as shown in FIGS. 5 and 6. Sleep appliance 74 has body 76. There are no wires or clasps to hold appliance 74 in place. Body 76 is made entirely from an acrylic plastic and made to fit over the upper posterior teeth to hold it in place, similar to an occlusal night guard. Anterior ramp 78, as in FIGS. 5 and 6, is wider than the ramp shown in FIGS. 1 and 2, extending across four maxillary teeth. Transpalatal bar 80, without projections in FIG. 7 and with projections 82, 84 and 86 in FIG. 8. extends across from posterior molars on one side to the other, to push the tongue down and open the airway.

Figure 9:
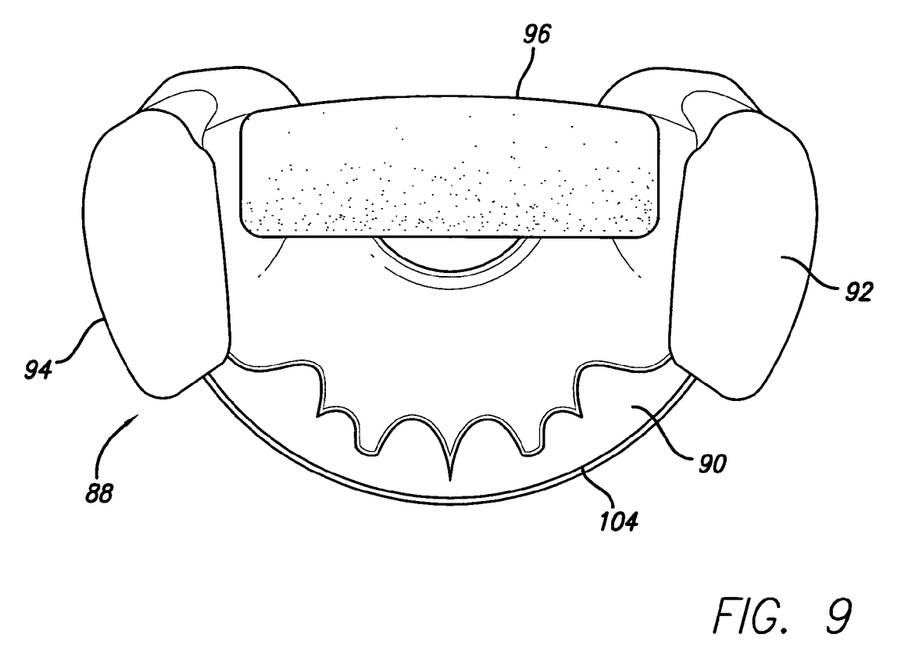
FIG. 9 is a bottom view of the embodiment of FIG. 1 with no anterior ramp and raised posterior ramps.
Figure 10:
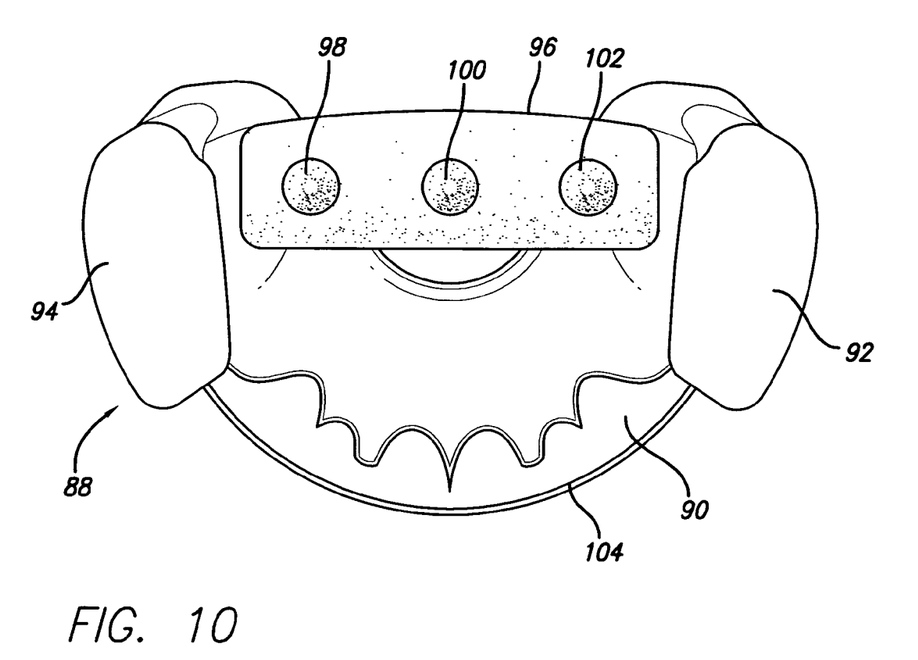
FIG. 10 is a bottom view of the embodiment of FIG. 9 with projections on the transpalatal bar.

Referring to FIGS. 9 and 10 there is shown another embodiment of the sleep appliance 88 having body 90. Body 90, in this embodiment, has no anterior ramp. There are two raised posterior ramps 92 and 94 against which the lower teeth occlude, to disclude the upper and lower teeth. The advantage of this embodiment is that the lack of the anterior ramp allows the tongue to come farther forward, which opens the airway even more. Transpalatal ramp 96 holds the tongue down to increase the airway. Transpalatal ramp 96 has projections 98, 100 and 102, shown in FIG. 10. Appliance 88 is held in place, as shown in FIGS. 1 and 2, by anterior retainer 104 and molar clasps, not seen, as they are hidden by posterior ramps 92 and 94.

Figure 11:
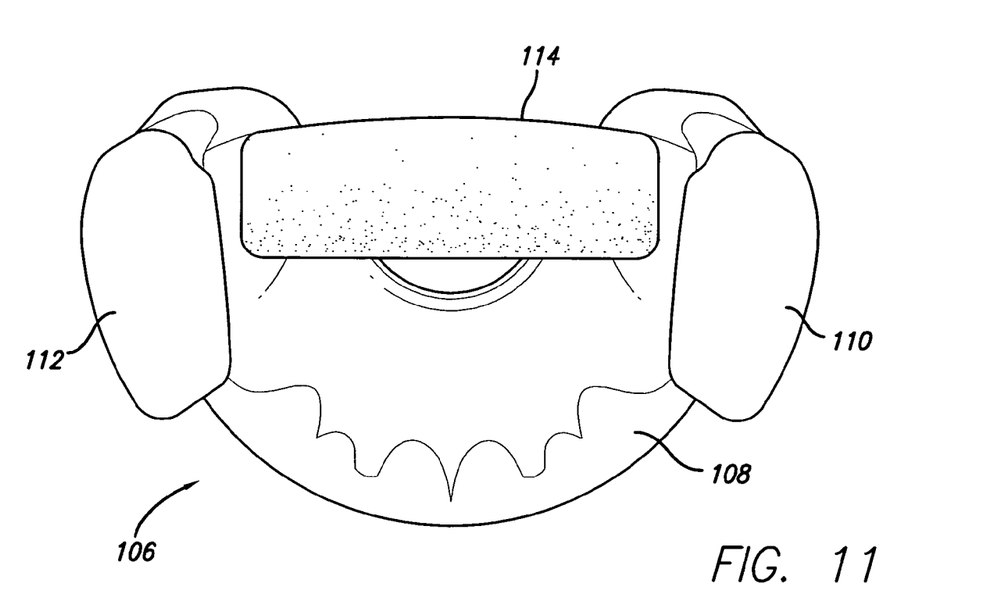
FIG. 11 is a bottom view of an embodiment with no anterior ramp and raised posterior ramps.
Figure 12:
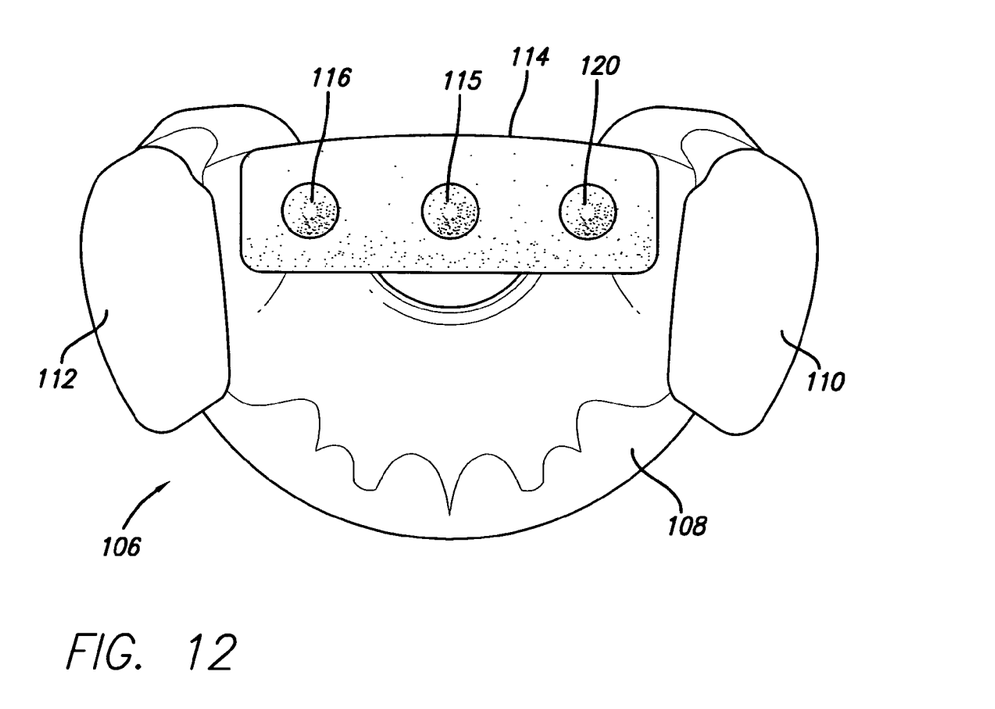
FIG. 12 is a bottom view of the embodiment of FIG. 11 with projections on the transpalatal bar.

Referring to FIGS. 11 and 12, sleep appliance 106 has body 108. There is no anterior ramp. Appliance 106 is all acrylic and fits as does an occlusal night guard, as described in FIGS. 3 and 4. Raised posterior ramps 110 and 112 provide a surface against which the lower teeth occlude. Transpalatal ramp 114 holds the tongue down to increase the airway. With no anterior ramp, the tongue can come forward increasing the airway flow. Raised projections 116, 118 and 120 are shown in FIG. 12.

Figure 13:
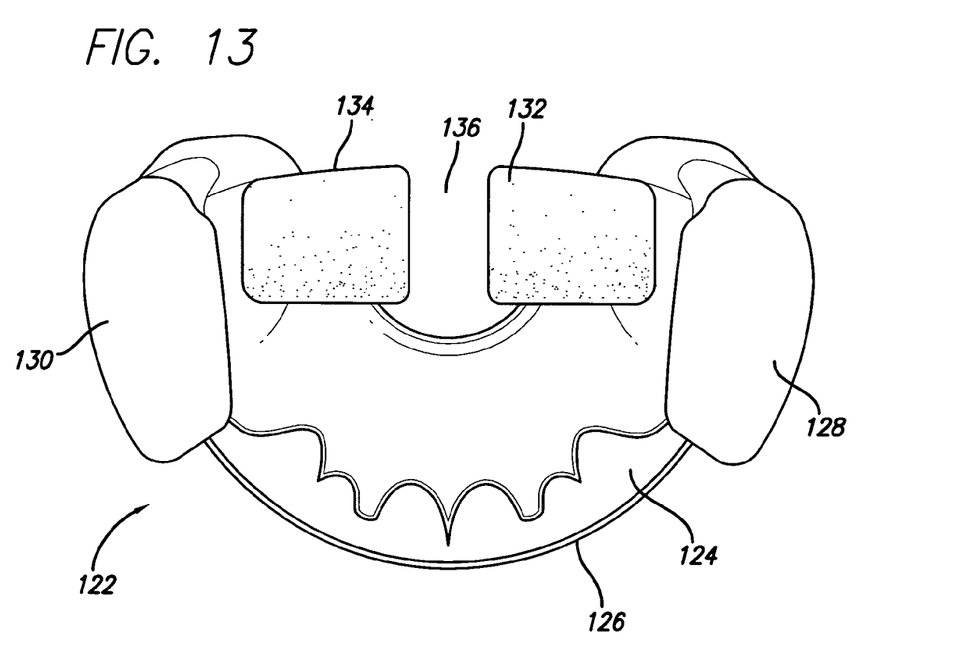
FIG. 13 is a bottom view of an embodiment with an open transpalatal bar.
Figure 14:
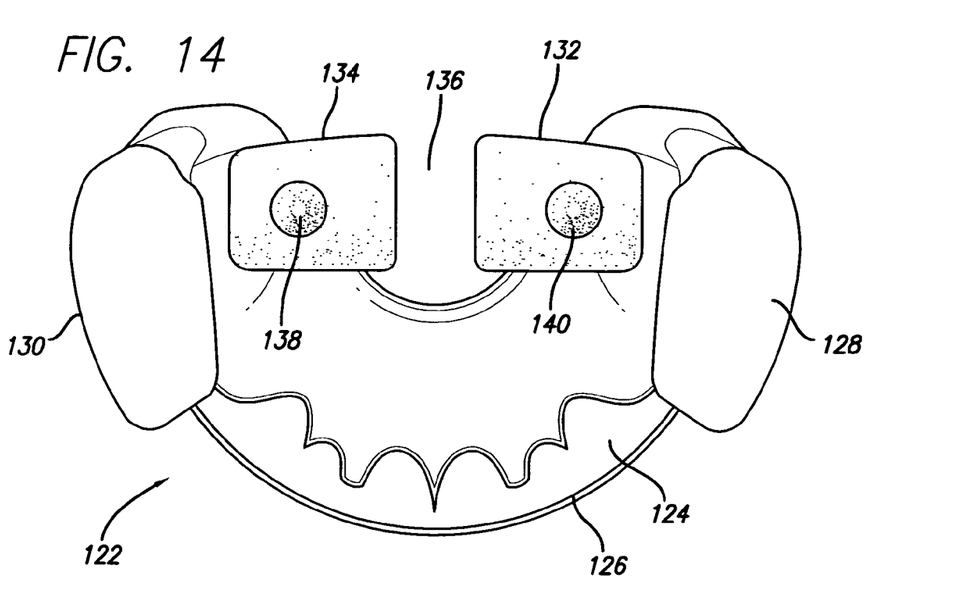
FIG. 14 is bottom view of the embodiment of FIG. 13 with projections on the transpalatal bar sections.

Referring to FIGS. 13 and 14 there is sleep appliance 122 with body 124. Appliance 122 is held in place by anterior retainer 126 and molar clasps, as in FIGS. 1 and 2. These clasps are not shown as they are hidden under posterior ramps 128 and 130. In this embodiment, there is no anterior ramp. The transpalatal ramp is split into and consists of two portions 132 and 134 creating a space 136, from about ¼ to about ½ inch wide between the two portions 132 and 134 of the transpalatal ramp. The extra space 136 provides a further opening of the airway than when a solid transpalatal ramp is used. The tongue is still held down but additional space exists for the airway. Projections 138 and 140 are present, as shown in FIG. 14, on portions 132 and 134.

The split transpalatal ramp may also be used on the all acrylic appliance that has no wires, as shown in FIG. 3.

Having thus described the invention, it is requested that the invention be described by the scope of the following claims.

I claim:

1. A dental oral appliance to open the airway for a sleeping individual who suffers with snoring or obstructive sleep apnea comprising, a body having an open palate, an occlusal coverage to removably affix the appliance to the upper teeth, structure configured to prevent occlusion of the upper and lower teeth, a transpalatal member, configured to provide a gap between the transpalatal member and the palate, that extends from the inside of the upper right molars to the inside of the upper left molars to inhibit the backward and upward movement of the tongue during sleep further comprising a plurality of raised projections on the bottom of the transpalatal member.

2. The dental oral appliance of claim 1 in which the transpalatal member comprises two portions with a space between the two portions.

3. The dental oral appliance of claim 1 in which the body is made of acrylic plastic.

4. The dental oral appliance of claim 1 in which the entire appliance is made of an acrylic plastic.

5. A dental oral appliance to open the airway for a sleeping individual who suffers with at least one of snoring and obstructive sleep apnea, comprising:
a body;
structure configured to removably affix the appliance to the upper teeth;
structure configured to prevent occlusion of the upper and lower teeth;
a transpalatal member configured to provide a gap between the transpalatal member and the palate, extending from the inside of the upper right molars to the inside of the upper left molars, to restrain the tongue from upward and backward movement; and,
a plurality of raised projections on the bottom of the transpalatal member.

6. The dental oral appliance of claim 5 in which the structure to removably affix the appliance to the upper teeth comprises an occlusal coverage.

7. The dental oral appliance of claim 5 in which the structure to prevent occlusion of the upper and lower teeth comprises a raised incisor ramp that extends from two or more incisors to the lingual.

8. The dental oral appliance of claim 5 in which the structure to prevent occlusion of the upper and lower teeth comprises raised posterior ramps.

9. The dental oral appliance of claim 5, in which the body has a series of recesses which fit against the lingual side of the upper teeth.

10. The dental oral appliance of claim 5 in which the body is made of clear acrylic plastic.

11. The dental oral appliance of claim 5 in which the entire appliance is made of an acrylic plastic.

12. The dental oral appliance of claim 5 in which the transpalatal member comprises two portions with a space between the two portions.

13. A dental oral appliance to open the airway for a sleeping individual who suffers with at least one of snoring and obstructive sleep apnea, comprising:
a body;
an occlusal coverage configured to removably affix the appliance to the upper teeth;
a raised incisor strip that extends from the incisal tip of two or more incisors to the lingual to prevent occlusion of the upper and lower teeth;
a transpalatal member configured to provide a gap between the transpalatal member and the palate, extending from the inside of the upper right molars to the inside of the upper left molars, to restrain the tongue from upward and backward movement; and,
a plurality of raised projections on the bottom of the transpalatal member.

14. A dental oral appliance to open the airway for a sleeping individual who suffers with at least one of snoring and obstructive sleep apnea, comprising:
a body;
an occlusal coverage configured to removably affix the appliance to the upper teeth;
raised posterior ramps to prevent occlusion of the upper and lower teeth;
a transpalatal member configured to provide a gap between the transpalatal member and the palate, extending from the inside of the upper right molars to the inside of the upper left molars, to restrain the tongue tram upward and backward movement; and,
a plurality of raised projections on the bottom of the transpalatal member.

* * * * *